United States Patent [19]

Ohno et al.

[11] 4,001,390
[45] Jan. 4, 1977

[54] METHOD OF COATING PHARMACEUTICAL SOLID DOSAGE FORMS

[75] Inventors: Shigeru Ohno, Kamakuna; Fujio Sekigawa, Yono; Shokichi Yamagishi, Omiya, all of Japan

[73] Assignee: Shin-Etsu Chemical Co., Ltd., Tokyo, Japan

[22] Filed: Apr. 1, 1975

[21] Appl. No.: 563,979

[30] Foreign Application Priority Data

Apr. 4, 1974 Japan .................... 49-38128

[52] U.S. Cl. .................... 424/35; 424/32; 424/33
[51] Int. Cl.² .................... A61K 9/32; A61K 9/36
[58] Field of Search .................... 424/32–35; 427/3

[56] References Cited

UNITED STATES PATENTS

| | | | |
|---|---|---|---|
| 2,816,062 | 12/1957 | Doerr et al. | 424/35 X |
| 2,881,085 | 4/1959 | Endicott et al. | 424/35 X |
| 3,043,747 | 7/1962 | Long | 424/35 X |
| 3,256,111 | 6/1966 | Singiser | 424/35 X |
| 3,371,015 | 2/1968 | Sjogren et al. | 424/35 X |
| 3,383,236 | 5/1968 | Brindamour | 424/35 X |
| 3,420,931 | 1/1969 | Daum et al. | 424/33 |
| 3,477,864 | 11/1969 | Tuji | 424/35 X |
| 3,576,663 | 4/1971 | Signorino et al. | 424/35 X |

*Primary Examiner*—Shep K. Rose
*Attorney, Agent, or Firm*—Toren, McGeady and Stanger

[57] ABSTRACT

Pharmaceutical solid dosage forms are covered with three successive layers of coating, consisting alternately of an undercoat composed substantially of a polymeric substance, a secondary coat composed substantially of a polymeric substance and a pigment, and a finish coat composed substantially of a polymeric substance. Application of these coatings produce economical advantages both in time and labor, and the surfaces of the coated dosage forms are smooth and glossy, and have no cracking.

3 Claims, No Drawings

METHOD OF COATING PHARMACEUTICAL SOLID DOSAGE FORMS

FIELD OF THE INVENTION

The present invention relates to pharmaceutical solid dosage forms, such as, tablets, pills, granules, and the like, covered with three successive layers of coatings.

DESCRIPTION OF THE PRIOR ART

Application of film coatings to various medical tablets, pills, granules and the like for purposes of protecting their ingredients from atmospheric moisture, masking any unpleasant color, taste and odor, and improving their outside appearance to increase their commerical value has been carried out in a variety of manners and by use of various compositions comprising polymeric substances, such as, cellulose derivatives and vinyl polymers. Since hiding the unpleasant color is the most important purpose of coating, it has been usual to coat the surfaces of tablets with a compositon comprising a polymeric substance and edible coloring agents, i.e., dyes and/or pigments, such as, titanium dioxide and aluminum lakes mixed in suitable proportions. In this case, however, when the pigments are used in increased proportions so that satisfactory covering or masking may be attained with a coating layer as thin as possible, the resulting coatings will produce a rough and lusterless layer or film which is very brittle and apt to crack by pressure or a blow during and after the coating process. On the other hand, when the loading of the pigment is low in the coating compositions, the resulting coating layer must be extraordinarily thick so as to sufficiently hide the unpleasant color of the substrate surfaces, and the use of such thick layer of coating means an economical disadvantage due to a great loss in time and labor.

OBJECTS OF THE INVENTION

It is an object of this invention to provide layers or films over the surfaces of tablets, pills, granules, and other pharmaceutical solid dosage forms with unpleasant colors, using small amounts of a coating material to form very thin coating layers having sufficient hiding power and which are capable of achieving a glossy and pretty finish.

SUMMARY OF THE INVENTION

According to the present invention, pharmaceutical solid dosage forms are covered with three successive layers of coating, consisting of a first or undercoat composed substantially of a polymeric substance, a secondary coat composed substantially of a polymeric substance and a pigment, and a third or finish coat composed substantially of a polymeric substance.

DETAILED DESCRIPTION OF THE INVENTION

It is well known that sufficient hiding power is exhibited on the surface of solid dosage forms by a coating layer of relatively small thickness when the material of the coating layer contains a high loading of pigments. However, such a coating layer is brittle and tends to crack under pressure and or blow during and after the coating process. In addition, the surface of such a layer is rough and lacks gloss. Furthermore, adhesion between the substrate surface and the coating material is poor, leading to peeling of the coating layer from the substrate surface.

The present invention is based on the discovery by the inventors that satisfactory results are obtained in the coating of solid dosage forms when the coating step using a coating material containing pigments in a very high loading is preceded by a coating step using a polymeric substance containing no pigments and is followed by a finishing step using a polymeric substance containing little or no pigment Thus, the problems of poor adhesion between the coating layer and the substrate surface and the poor outer appearance and the poor mechanical properties of the coating layers can be simultaneously solved, while providing sufficient covering of the substrate surface with very thin coating layers which gives economical advantages in both time and labor.

The first or undercoat layer covering the solid dosage forms according to the method of the invention is made from a composition composed substantially of a known polymeric substance that is usually employed as the base material for forming coating films. To this composition, anti-oxidants, plasticizers, flavorings, and the like as well as auxiliary additives may be added in a small amount.

The second or middle layer applied over the above-described undercoat is formed from a composition comprising one or more of coloring agents including inorganic pigments, such as, titanium dioxide, talc, precipitated calcium carbonate, calcium sulfate, and edible lake pigments, and edible dyes, and a film-forming polymeric substance. This coating composition may additionally contain auxiliary additives, such as, plasticizers and flavorings.

Next, the third or finish coat applied over the above second layer is composed substantially of the polymeric substance, as in the undercoat. It is possible to incorporate dyes, plasticizers, sweetenings and flavorings in a small amount. Pigments can also be included in the finish coat layer in an amount not exceeding 10% by weight of the polymeric substance.

The polymeric substances that are used for the preparation of the treble layers are known, and are exemplified by the following: cellulose derivatives readily dissolving in the stomach, such as, hydroxypropylmethylcellulose, hydroxypropylcellulose, methylcellulose, and hydroxyethylcellulose; vinyl derivatives readily dissolving in the stomach, such as, polyvinylpyrrolidone, vinylpyrrolidone-vinylacetate copolymer, polyvinylacetal-diethylaminoacetate copolymer, dimethylaminoethylmethacrylate-methylmethacrylate copolymer, and 2-methyl-5-vinylpyridinium-methyacrylate-methacrylic acid copolymer; cellulose derivatives readily dissolving in the intestines, such as, cellulose acetate phthalate, hydroxypropyl methylcellulose phthalate, cellulose-acetate hexahydrophthalate, and hydroxypropyl methylcellulose hexahydrophthalate; vinyl derivatives readily dissolving in the intestines, such as, methylmethacrylatemethacrylic acid copolymer; and film-forming compounds soluble in organic solvents, such as, ethylcellulose, shellac, polyvinylacetate, and acetylcellulose.

When the coating compositions are formulated for the purpose of forming the treble layers on the solid dosage forms, it is convenient to use the identical polymeric substances although it is also possible to use a different one for each layer.

In the formulation of the coating compositions according to the present invention, water or any one of a member of organic solvents capable of dissolving the polymeric substance, or a mixture thereof may be employed so that a solid content of from about 2 to about 20% be weight may be obtained. Illustrative of such organic solvents are methanol, ethanol, isopropanol, methylene chloride, 1,1,1-trichloroethane, trichloroethylene, dichloroethylene, ethylacetate, acetone, methylethylketone, and mixtures thereof.

Further, in the formulation of the coating composition suitable for the second layer, the ratio of the polymeric substance and the pigment is usually between 5:1 and 1:5 by weight, depending on the kind of polymeric substances used, the degree of polymerization thereof, and the kind of pigments used.

Each of the treble layers can be formed by a conventional method of coating by use of, for example, pan coaters, fluidizing coaters and drum-type coaters. According to preferred embodiments of the invention, the first or undercoat layer can be as thin as from 0.01 to 0.04 mm, the secondary layer can be in a wide range of thickness of from 0.01 to 0.10 mm, and variable depending upon the nature of the substrate surfaces, to obtain a sufficient hiding effect. The third or finish coat layer can be as thin as from 0.01 to 0.03 mm to produce a sufficiently glossy and smooth surfaces. When good enteric solubility of the solid dosage forms is particularly required, the finish coat should be from 0.04 to 0.50 mm or more thick.

The following examples illustrate the present invention. In the examples parts are all parts based on weight.

EXAMPLE 1.

To a mixture of 60 parts of lactose and 40 parts of corn starch was added 15 parts of a 20% by weight ethanolic solution of polyvinylpyrrolidone (K-30), while to a mixture of 60 parts of lactose, 40 parts of corn starch, and 1 part of amaranth was added 15 parts of the same solution of polyvinylpyrrolidone, accompanied by kneading. The two resulting mixtures were fed to and passed through a granulator having a screan with openings 0.8 mm in diameter, followed by airdrying for 24 hours, to produce granules A and B.

100 parts of the above granules A and 100 parts of granules B were mixed togther, and to this mixture was added 1 part of magnesium stearate. The resulting material was then put in a rotary-type tabletting machine to manufacture tablets, each 9 mm in diameter and 290 mg in weight with surfaces bearing dappled reddish spots. The tablets thus obtained were then coated with two different coating solutions to form the treble coatings, by use of an automatic pan coating apparatus (FM-2, product of Freund Industry Corp., Japan) by the manner as set forth in the following.

For the making of the undercoat and finish coat according to the present invention, a coating solution composed of 8 parts of hydroxypropylmethyl cellulose (Pharmacoat-606, manufactured by Shin-Etsu Chemical Co., Japan), 50 parts of methylene chloride, and 42 parts of ethanol were used. For the making of the middle coat containing the pigmentary ingredients, a coating solution composed of 8 parts of the same hydroxypropylmethyl cellulose, 12 parts of titanium dioxide, 1 part of tartrazine aluminum lake, 50 parts of methylene chloride, and 42 parts of ethanol were used. On each coat, 2 kg, of the above tablets were charged in the pan coater, and each coating was carried out with repeated cycles of spraying (solution temperature: 25° C) for 10 seconds and drying (blowing air temperature: 40° C) for 30 seconds. The results are set out in Table I, together with the results of 2 controls undertaken with or without the undercoat and without the finish coat.

Table I

| | Present Invention | Control 1 | Control 2 |
|---|---|---|---|
| Undercoat | Thickness: 0.02 mm Quantity: 3.4 mg/ tablet | * | Thickness: 0.02 mm Quantity: 3.4 mg/ tablet |
| Secondary coat | Thickness: 0.03 mm Quantity: 12.8 mg/ tablet | Thickness: 0.03 mm Quantity: 12.8 mg/ tablet | Thickness: 0.03 mm Quantity: 12.8 mg/ tablet |
| Finish coat | Thickness: 0.01 mm Quantity: 1.7 mg/ tablet | * | * |
| Outer appearance of coated tablets | No cracking. Smooth and glossy. | Cracking occurring to about 80% of products | No cracking. Smoothness lacking. Not glossy. |

* No coating was carried out.

It is evident from the above table that cracking in the surfaces of coated tablets occurs when no undercoating is applied and can be completely prevented by the application of undercoating, and also that the finish coating contributes to the sufficient smoothness and gloss of the coated tablet surfaces.

It should be added in connection with the above tests that the specified quantity of the secondary coat was enough to entirely hide any colored spots.

EXAMPLE 2.

The same tablets as used in Example 1 were coated, using the following three different coating solutions A, B, and C.

Solution A:
Hydroxypropylmethyl cellulose (Pharmacoat-606, of Shin-Etsu Chemical Co., Japan)    8 parts
Methylene chloride    46 parts
Methanol    46 parts Solution B:
The same hydroxypropylmethyl cellulose as above    8 parts
Titanium dioxide    12 parts
Indigo Carmine aluminum lake    1 part
Methylene chloride    46 parts
Methanol    46 parts Solution C:
The same hydroxypropylmethyl cellulose as above    8 parts
Indigo Carmine aluminum lake    0.2 part
Methylene chloride    46 parts
Methanol    46 parts Solution D:
The same hydroxypropylmethyl cellulose as above    8 parts
Titanium dioxide    4 parts
Indigo Carmine aluminum lake    0.3 part
Methylene chloride    46 parts
Methanol    46 parts Solution A was applied as the undercoating, Solution B was applied as the secondary coating, while Solution C as the finish coating, according to the procedure of Example 1. Solution D was applied for a single coat as a control. Solutions B and D were used in quantities enough for entirely hiding surfaces under. The results are set out in the following Table II.

Table II

Quantity of Coat, mg/tablet

| | Hydroxy-propylmethyl-cellulose | Titanium dioxide | TOTAL | Thickness of Coat mm |
|---|---|---|---|---|
| Present invention: | | | | |
| Undercoat | 3.4 | | 3.4 | 0.02 |
| Secondary coat | 4.8 | 7.2 | 12 | 0.03 |
| Finish coat | 1.7 | | 1.7 | 0.01 |
| TOTAL | 9.9 | 7.2 | 17.1 | 0.06 |
| Control: | | | | |
| Single coat | 15 | 8 | 24 | 0.11 |

It was observed that the tablets coated with Solutions A, B and C above gave smoothness and much gloss to their surfaces, whereas those of a single coat of Solution D gave no gloss at all to their surfaces, though smoothness was given to some extent. Further, it is evident from the above table that hiding can be achieved by less quantities of coat by the treble layers of this invention, compared to the single coat.

EXAMPLE 3.

The same tablets as used in Example 1 were coated, using the following three different solutions, E, F, and G.

| | |
|---|---|
| Solution E: | |
| Hydroxypropylmethyl cellulose phthalate (product of Shin-Etsu Chemical Co., Japan, HPMCP, Grade: HP-55) | 10 parts |
| Methylene chloride | 45 parts |
| Ethanol | 45 parts |
| Solution F: | |
| Hydroxypropylmethyl cellulose phthalate (do.) | 10 parts |
| Titanium dioxide | 10 parts |
| Tartrazine aluminum lake | 1 part |
| Methylene chloride | 45 parts |
| Ethanol | 45 parts |
| Solution G: | |
| Hydroxypropylmethyl cellulose phthalate (do.) | 10 parts |
| Titanium dioxide | 1 part |
| Tartrazine aluminum lake | 0.2 part |
| Methylene chloride | 45 parts |
| Ethanol | 45 parts |

Each coating was carried out by a fluidizing coater of Model WSLD-3 of Fa. Werner Glatt, West Germany. Solution E was applied as the undercoating and finish coating, while Solution F was applied as the secondary coating, according to the procedure of Example 1. Solution G was applied for a single coat as a control. Solutions F and G were used in quantities sufficient to entirely hiding the surfaces. The finish coat of solution E was intended to have a thickness sufficient for an enteric coating. The results of these coating tests are set out in Table III.

Table III

| | Quantity of Coat, mg/tablet | | | Thickness of Coat mm |
|---|---|---|---|---|
| | Hydroxypropyl-methylcellulose phthalate | Titanium dioxide | TOTAL | |
| Present invention: | | | | |
| Undercoat | 3.4 | | 3.4 | 0.02 |
| Secondary coat | 5 | 5 | 10 | 0.03 |
| Finish coat | 12 | | 12 | 0.07 |
| TOTAL | 20.4 | 5 | 25.4 | 0.12 |
| Control: | | | | |
| Single coat | 35 | 3.5 | 38.5 | 0.21 |

It was found from the above table that the use of the hydroxypropylmethyl cellulose phthalate as the polymeric substance required a much decreased quantity for the treble coatings, compared to the single coat as a control, and further that the surfaces of tablets with the treble coatings were superior in their smoothness and gloss to the single coating.

The thus coated tablets were subjected to disintegration tests in accordance with the U.S. Pharmocopoeia XVIII. The results indicated that when the simulated gastric fluid was used, they showed no evidence of disintegration, cracking, or softening, whereas, when the simulated intestinal fluid was used, the tablets with the treble coatings disintegrated completely in 8 minutes and 45 seconds, while those with the single coating disintegrated completely in 10 minutes and 55 seconds. In the simulated gastric fluid test, the simulated gastric fluid which permeated into the triple-coated and single coated tablets was equivalent to 1.6% and 1.7% of the weight of the tablets, respectively, or was approximately the same.

What is claimed is:

1. A pharmaceutical solid dosage form coated with three successive layers comprising:
   1. an inside layer closest to said solid dosage form containing no pigment and consisting of hydroxy propylmethyl cellulose or hydroxy propylmethyl cellulose phthalate;
   2. a layer over layer (1) consisting of said polymer and a pigment; and
   3. an outer layer over layer (2) consisting of said polymer and up to 10 weight percent pigment based on the weight of said polymer.

2. A pharmaceutical solid dosage form coated with three successive layers comprising:
   1. an inside layer closest to said solid dosage form consisting of hydroxy propylmethyl cellulose and containing no pigment;
   2. a layer over layer (1) consisting of hydroxy propylmethyl cellulose and a pigment; and
   3. an outer layer over layer (2) consisting of hydroxy propylmethyl cellulose and up to 10 weight percent pigment based on the weight of the hydroxy propylmethyl cellulose.

3. The pharmaceutical solid dosage form as claimed in claim 2 wherein said layer (2) contains said hydroxy propylmethyl cellulose and said pigment in a ratio of from 5:1 to 1:5 by weight.

* * * * *